(12) United States Patent
Caro et al.

(10) Patent No.: US 8,808,354 B2
(45) Date of Patent: Aug. 19, 2014

(54) HELICAL STENT

(75) Inventors: Colin Gerald Caro, London (GB); Ioannis Petousis, London (GB); Brian G. Falzon, London (GB)

(73) Assignee: Veryan Medical Limited, Oxford (GB)

( * ) Notice: Subject to any disclaimer, the term of this patent is extended or adjusted under 35 U.S.C. 154(b) by 0 days.

(21) Appl. No.: 13/567,466

(22) Filed: Aug. 6, 2012

(65) Prior Publication Data

US 2014/0039605 A1    Feb. 6, 2014

Related U.S. Application Data

(63) Continuation of application No. 11/663,400, filed as application No. PCT/GB2005/003665 on Sep. 22, 2005, now Pat. No. 8,236,043.

(30) Foreign Application Priority Data

Sep. 22, 2004    (GB) .................................. 0421085.2

(51) Int. Cl.
     *A61F 2/06*      (2013.01)
(52) U.S. Cl.
     USPC ....................................................... 623/1.22
(58) Field of Classification Search
     USPC ....................................................... 623/1.22
     See application file for complete search history.

(56) References Cited

U.S. PATENT DOCUMENTS

| 5,449,373 | A | 9/1995 | Pinchasik et al. |
| 5,749,919 | A | 5/1998 | Blanc |
| 5,800,456 | A | 9/1998 | Maeda et al. |
| 6,183,506 | B1 | 2/2001 | Penn et al. |
| 6,270,524 | B1 | 8/2001 | Kim |
| 6,432,127 | B1 | 8/2002 | Kim et al. |
| 6,572,646 | B1 | 6/2003 | Boylan et al. |
| 8,066,761 | B2 | 11/2011 | Caro et al. |
| 2002/0007212 | A1 | 1/2002 | Brown et al. |
| 2002/0179166 | A1 | 12/2002 | Houston et al. |

(Continued)

FOREIGN PATENT DOCUMENTS

| EP | 1 279 382 A1 | 1/2003 |
| GB | 2 344 053 A | 5/2000 |

(Continued)

OTHER PUBLICATIONS

International Search Report of International Appl. No. PCT/GB2005/003665 dated Dec. 2, 2005, 2 pages.

(Continued)

*Primary Examiner* — David Isabella
*Assistant Examiner* — Jacqueline Woznicki
(74) *Attorney, Agent, or Firm* — Fay Sharpe LLP

(57) ABSTRACT

A stent for insertion in a fluid conduit of a human or animal body includes a hollow structure having generally circumferentially extending parts which have opposite end portions in the longitudinal direction. The circumferential parts are joined to a longitudinally adjacent circumferential parts along the length of the hollow structure wherein the end portions of adjacent circumferential parts are not in parallel planes and/or the end portions of the same part are not in parallel planes. Also, the non-parallel end portions are arranged along the length of the hollow structure such that a flow lumen defined by the hollow structure, and imposed on the flow lumen by the hollow structure when in the fluid conduit, follows a non-planar curve.

13 Claims, 6 Drawing Sheets

(56) References Cited

U.S. PATENT DOCUMENTS

2004/0215319 A1  10/2004  Berra et al.
2005/0149168 A1  7/2005   Gregorich
2006/0265051 A1  11/2006  Caro et al.
2008/0262599 A1* 10/2008  Caro et al. .................. 623/1.16

FOREIGN PATENT DOCUMENTS

| | | |
|---|---|---|
| JP | 2000-279530 | 10/2000 |
| WO | WO 98/53764 | 12/1998 |
| WO | WO 00/38591 | 7/2000 |
| WO | WO 03/045279 A1 | 6/2003 |
| WO | WO 03/056228 A1 | 7/2003 |

OTHER PUBLICATIONS

British Search Report of British Appl. No. GB0421085.2, dated Dec. 8, 2004, 1 page.

* cited by examiner

HELICAL STENT

This application is a continuation of U.S. application Ser. No. 11/663,400 filed on Jan. 14, 2008 and issued as U.S. Pat. No. 8,236,043 on Aug. 7, 2012. Application Ser. No. 11/663,400 is a 371 of PCT/GB05/03665 filed Sep. 22, 2005.

This invention relates to stents for insertion in a fluid conduit of the human or animal body.

Stents are generally tubular devices used for providing physical support to blood vessels, i.e. they can be used to help prevent kinking or occlusion of blood vessels such as veins or arteries and to prevent their collapse after dilatation or other treatment.

Stents can be broadly divided into two main categories: balloon expandable stents and self-expanding stents. In the case of the former the material of the stent is plastically deformed through the inflation of a balloon, so that after the balloon is deflated the stent remains in the expanded shape. Such stents are manufactured in the "collapsed" condition, ready for delivery, and may be expanded to the expanded condition when inside the vessel or other fluid conduit.

Self-expanding stents are also designed to be delivered in the collapsed condition and when released from a constraining delivery system the stent expands to its expanded condition of a predetermined size. This effect is achieved by using the elasticity of the material and/or a shape-memory effect. In the case of shape-memory stents a commonly used material is nitinol.

Many different designs of stents are available on the market. They are made from a variety of materials providing corrosion resistance and biocompatibility. They are made from sheet, round or flat wire or tubing. They are generally cylindrical but also longitudinally flexible so as to conform to the curvature of the fluid conduit into which they are inserted.

We have previously proposed that the flow pattern in arteries including the swirling pattern induced by their non-planar geometry operates to inhibit the development of vascular diseases such as thrombosis, atherosclerosis and intimal hyperplasia.

In WO 98/53764, there is disclosed a stent for supporting part of a blood vessel. The stent includes a supporting portion around which or within which part of a blood vessel intended for grafting can be placed so that the stent internally or externally supports that part. The supporting portion of the stent is shaped so that flow between graft and host vessel is caused to follow a non-planar curve. This generates a swirl flow, to provide a favourable blood flow velocity pattern which reduces the occurrence of vascular disease, particularly intimal hyperplasia.

In WO 00/32241, there is disclosed another type of stent, in this case including a supporting portion around which or within which part of an intact blood vessel other than a graft can be placed. This supporting portion can prevent failure of the vessel through blockage, kinking or collapse. Again, the supporting portion of the stent is of a shape and/or orientation whereby flow within the vessel is caused to follow a non-planar curve. Favorable blood flow velocity patterns can be achieved through generation therein of swirl flow within and beyond the stent. Failures in blood vessels through diseases such as thrombosis, atherosclerosis, intimal hyperplasia can thereby be significantly reduced.

Further aspects of how swirl flow is beneficial are explained in the above publications. It is further explained in Caro et al. (1998) J. Physiol. 513P, 2P how non-planar geometry of tubing inhibits flow instability.

We have now found a way of producing an internal stent which facilitates flow within the stent supported fluid conduit to follow a non-planar curve, i.e. to swirl.

According to a first aspect of the invention there is provided a stent for insertion in a fluid conduit of the human or animal body, comprising a hollow structure having generally circumferentially extending parts which have opposite end portions in the longitudinal direction, the circumferential parts being joined to longitudinally adjacent circumferential parts along the length of the hollow structure, wherein the end portions of adjacent circumferential parts are not in parallel planes and/or the end portions of the same part are not in parallel planes, and wherein the non-parallel end portions are arranged along the length of the hollow structure such that a flow lumen defined by the hollow structure and imposed on the flow lumen by the hollow structure when in the fluid conduit follows a non-planar curve.

In use, when the stent is in its expanded condition in a fluid conduit, it will define and impose a non-planar flow lumen therein. Flow within the fluid conduit supported by the stent will then follow a non-planar curve, promoting swirl flow, the benefits of which are discussed above. Thus, considering the flow lumen of the conduit, as this extends in the longitudinal direction (x-axis) it curves in more than one plane (i.e. in both the y-axis and the z-axis). In other words, the flow lumen extends generally helically in the longitudinal direction.

Stents are known which are designed to flex and adopt the flow lumen curvature of the vessel in which they are inserted. It is possible that such stents, when inserted in a natural non-planar vessel, will be caused to adopt a non-planar shape themselves. However, in contrast, the stent of the present invention is pre-shaped to incorporate the non-planar curve. Once installed in the fluid conduit it imposes on that conduit the non-planar curve with which it has been pre-shaped, subject to minor variations caused by the respective stiffness of the conduit wall, the surrounding tissue and the hollow structure of the stent. The natural shape of the stent (i.e. with no external stresses such as those holding the stent in a deployment device) is such as to provide a non-planar flow lumen.

Preferably, the centre line of the stent in the expanded condition follows a substantially helical path. In other words, the centroids of adjacent cross-sectional slices through the stent define a helical locus or centre line.

The invention is applicable to stents internal to intact blood vessels or blood vessels intended for grafting.

When the stent is in its expanded condition, it causes the fluid conduit to follow a non-planar curve as it extends in the longitudinal direction. Preferably, the curve undergoes at least one turn. The provision of more than one turn, more preferably a plurality of turns, is enabled by the ability of preferred stents to expand from the collapsed condition to the expanded condition without substantial twisting, i.e. there is no significant rotation of one end of the stent relative to the other. This can be achieved by the hollow structure of the stent having the same number of turns both when the stent is collapsed and when it is expanded. This property of the stent means that it can expand without causing the conduit to twist, which would be undesirable because of the tethering of the conduit in the human or animal body.

The circumferentially extending parts of the hollow body may, in certain embodiments, be endless tubular parts. By arranging a series of tubular parts end to end in a row, the hollow structure of the stent may be defined.

Each tubular part may have a long side and a short side diametrically opposite to the long side, with the long side of each tubular part being rotationally offset from the long side of the next longitudinally adjacent tubular part. In this way the tubular parts can create a non-planar flow lumen. The centre line of the hollow structure may follow a substantially helical path, even though the centre line of each individual tubular part has a straight centre line. In these embodiments the end portions of the same tubular part are not in parallel planes. When viewed in side elevation, the tubular parts are generally "wedge" shaped. In an example, the rotational offset between a tubular part and the next tubular part may be 10°, so that after 36 tubular parts the helix of the flow lumen has undergone one complete turn of 360°.

The tubular parts may be directly connected to each other with no longitudinal spacing therebetween. Preferably, however, the tubular parts are longitudinally spaced from each other and joined together by connecting means. Such connecting means may take the form of a plurality of struts arranged around the circumference of the hollow structure.

The connecting means may be of the same length around the circumference of the hollow structure, for example interconnecting the wedge-shaped tubular parts described above. Alternatively, the connecting means may have a long length on one side of the hollow structure and a short length on the other, diametrically opposite side of the hollow structure. The long length of each connecting means is preferably then rotationally offset from the long length of the next longitudinally adjacent connecting means. In this arrangement, the end portions of adjacent circumferential parts are not in parallel planes, because the connecting means "tilts" the adjacent parts relative to each other. Each tubular part may itself then have its end portions arranged parallel to each other. Alternatively the tubular parts could be both "wedge" shaped and interconnected by connecting means of long and short length, with the respective "non-parallel" features preferably complimenting each other to create the non-planar curve of the hollow structure.

If the connecting means is in the form of a set of struts, the struts may extend circumferentially (i.e. laterally on the surface of the hollow structure) as well as longitudinally. It is preferred for a set of struts which connect adjacent circumferential parts to each other to include at least one strut oriented in a first lateral direction as well as longitudinally and at least one strut oriented in a second lateral direction as well as longitudinally. This can help to ensure that the desired longitudinal spacing between the adjacent circumferential parts is achieved by the set of struts, by avoiding significant relative twisting of the circumferential parts.

The circumferentially extending parts may, in certain embodiments, be turns belonging to a single helical coil extending circumferentially and longitudinally of the hollow structure. Since the hollow structure of the strut provides a non-planar (i.e. helical) flow lumen, these embodiments in effect are in the form of "coiled coils". The single helical coil forms the wall of the hollow structure. The helical coil may take the form of a "strip" of closed cells or of a zig-zag shaped wire or bar. Helical coil stents forming cylindrical structures are known. However, in one form of helically coiled stent embodying the invention, the width of the helical coil varies along the length of the coil. Thus, the opposite end portions in the longitudinal direction of a given turn of the coil (e.g. the opposite edges of a strip shaped coil) will not be in parallel planes.

The turns of the helical coil may be longitudinally spaced from each other and joined together by connecting means. The connecting means may be of the same length around the circumference of a turn, for example interconnecting a helical coil of varying width as described above. Alternatively, the connecting means may have a long length on one side of the hollow structure and a short length on the other, diametrically opposite side of the hollow structure. The long length of each connecting means is preferably then rotationally offset from the long length of the next longitudinally adjacent connecting means. In this arrangement, the end portions of adjacent turns of the helical coil are not in parallel planes, because the connecting means "tilts" the adjacent turns relative to each other. The helical coil may then be of constant width, so that the opposite end portions (e.g. the opposite edges of a strip shaped coil) will be in parallel planes. Alternatively the helical coil could be both of variable width and interconnected by connecting means of long and short length, with the respective "non-parallel" features preferably complimenting each other to create the non-planar curve of the hollow structure.

It is generally preferred to avoid any pronounced grooves, ridges, ribs or vanes in the hollow structure of the stent, as these may have the opposite of the desired effect of improving flow characteristics, i.e. they may obstruct the flow, facilitate deposit build up or create stagnant regions. Preferably, therefore, the stent is substantially free of ribs or vanes, for example free of thicker wires (than adjacent wires) which would act as a rib projecting into the flow lumen of the fluid conduit. Where connecting means e.g. struts are provided, the connecting means may be radially outwardly displaced from the circumferential parts to assist anchoring in the fluid conduit.

The stent improves flow characteristics. As is well known, in the case of straight tubes, near wall velocities are very low compared to velocities at the core of the tube, due to the effects of viscosity. In the case of tubes which are bent in a single plane, the speed of the flow at the outside of the bend is increased but the speed of the flow at the inside is retarded further. In both cases, in inertially dominated flows such as in arteries, there is considerable variation in axial velocity across the width of the tube. With the use of a non-planar flow lumen swirl flow is generated and the axial velocity profile of the flow across the fluid conduit becomes generally more uniform or "blunter", with the axial velocity of flow at both the outside and inside of the fluid conduit being closer to the mean axial velocity.

Thus, the flow characteristics are improved by causing swirling and a relatively uniform distribution of axial and near wall velocity. Mixing over the cross section is also promoted and there is a reduction in the likelihood of occurrence of flow instability. The avoidance and flushing of stagnant zones is assisted. There is a reduction in the potential for deposit build up within and downstream of the graft and the development of pathology.

The amplitude and pitch of the helical centre line may be chosen to vary along the length of the stent, if desired. Variation of amplitude can be achieved by increasing or decreasing the angle between the non-parallel planes, whilst variation in pitch may be achieved by varying the amount of rotational offset between adjacent pairs of non-parallel planes. Such variations may for example be desired if it is wished to introduce a gentle swirl at the upstream end of the stent and to increase the swirl effect in the downstream direction.

The stent may be of the self-expanding type or it may be balloon expandable.

The basic geometry of the stent may be of the many available types, such as coil stents, helical spiral stents, woven stents, sequential ring stents, closed cell sequential ring stents, and open cell stents. They may be made by coiling, braiding or knitting wires, by laser cutting from tubing, by electric discharge milling (EDM), by chemical etching or by other known methods. They may be made from a variety of materials, including stainless steel, nitinol, tantalum, platinum iridium, niobium alloy, cobalt alloy or polymers (such as biodegradable polymers).

In certain aspects, the invention is concerned with stents for insertion in flexible conduits of the human or animal body, in which a helical centre line of the flow lumen of the fluid conduit is of relatively small amplitude.

Preferably the flow lumen defined by the hollow body has a centre line which follows a substantially helical path, the helical centre line having a helix angle less than or equal to 65° and an amplitude less than or equal to one half of the internal diameter of the flow lumen.

In this specification, the amplitude of the helix refers to the extent of displacement from a mean position to a lateral extreme. So, in the case of the flow lumen having a helical centre line, the amplitude is one half of the full lateral width of the helical centre line.

In the flow lumen, in which the amplitude of the helix is less than or equal to one half of the internal diameter of the flow lumen, there is a "line of sight" along the flow lumen, unlike in the case of a corkscrew configuration where in effect the helix is wound around a core (either solid, or "virtual" with a core of air). We have found that the flow at the line of sight generally has a swirl component, even though it could potentially follow a straight path.

For the purposes of this specification, the term "relative amplitude" of a helical flow lumen is regarded as the amplitude divided by the internal diameter. So, in the flow lumen in which the amplitude of the flow lumen is less than or equal to one half of the internal diameter of the flow lumen, this means that the relative amplitude is less than or equal to 0.5. Relative amplitudes less than or equal to 0.45, 0.4, 0.35, 0.3, 0.25, 0.2, 0.15 or 0.1 may be preferred in some circumstances. It is however preferred for the relative amplitude to be at least 0.05, more preferably 0.1. This can help to ensure that the desired swirl flow is induced.

The relative amplitude may vary according to the use of the stent and the spatial constraints on its design. It will however be appreciated that by keeping the amplitude less than half the flow lumen internal diameter a swirling flow may be induced without creating an excessively large device. The "envelope" occupied by the stented conduit can fit into the space available in the tissue surrounding the fluid conduit, and even if this envelope is caused to follow a particular path by the local environment in which the conduit is located, the desired helical geometry of the flow lumen can be maintained.

It is expected that the conduit may prevent the stent from expanding to its full size. Therefore, the stent may be designed to have a relative amplitude greater than 0.5 (e.g. 0.6 or 0.7), but so that in use a relative amplitude of the flow lumen is equal to or less than 0.5. In certain preferred arrangements, however, the relative amplitude of the expanded stent ex vivo is less than or equal to 0.5.

The angle of the helix is also a relevant factor in balancing the space constraints on the flow tubing with the desirability of maximising the cross-sectional area available for flow. The helix angle is less than or equal to 65°, preferably less than or equal to 55°, 45°, 35°, 25°, 20°, 15°, 10° or 5°. As with relative amplitudes, the helix angle may be optimized according to the conditions: viscosity, density and velocity of fluid.

Generally speaking, for higher Reynolds numbers the helix angle may be smaller whilst satisfactory swirl flow is achieved, whilst with lower Reynolds numbers a higher helix angle will be required to produce satisfactory swirl. The use of higher helix angles will generally be undesirable, as there may be near wall pockets of stagnant fluid. Therefore, for a given Reynolds number (or range of Reynolds numbers), the helix angle will preferably be chosen to be as low as possible to produce satisfactory swirl. Lower helix angles result in smaller increases in length as compared to that of the equivalent cylindrical stent. In certain embodiments, the helix angle is less than 20° or less than 15°.

It will be appreciated that in pulsatile flow, the Reynolds number will vary over a range. Typical mean resting arterial blood flow Reynolds numbers are about 100 to 200, reaching peak values of two or three times that in pulsatile flow and three to four times the mean during exertion. Therefore the extent to which swirl flow is promoted will vary likewise. Even if there are stagnant flow regions at lower Reynolds numbers, because for example a low helix angle and/or a low relative amplitude has been selected, these will tend to be flushed out during periods of flow when the Reynolds numbers are higher.

For reasons of manufacturing simplicity, it may be preferred for the stent to have a substantially constant cross-sectional area along its length. There may be variations in use caused by loading on the stent.

The non-planar part of the stent may extend along just part of the overall length of the stent or it may extend over substantially its entire length. For example, a stent may define a non-planar flow lumen over part of its length or over substantially its entire length. Other properties of the stent may also vary over the length of the stent, for example structural properties such as stiffness.

The stent may undergo a fraction of one complete turn, for example one quarter, one half or three quarters of a turn. Preferably, the stent undergoes at least one turn, more preferably at least a plurality of turns. Repeated turns of the helix along the stent will tend to ensure that the swirl flow is generated and maintained.

The stent may extend generally linearly. In other words, the axis about which the centre line of the stent follows a substantially helical path, may be straight. Alternatively the axis may itself be curved, whereby the envelope occupied by the stented conduit is curved, for example to produce an "arch" shaped conduit. The bend of the arch may be planar or non-planar, but should preferably be such that swirl is maintained and not cancelled by the geometry of the bend. Thus, for example, a stent may be generally "arch" shaped (planar or non-planar), having the generally circumferentially extending parts arranged in accordance with the invention to produce a non-planar flow lumen.

The stent may if desired comprise a pharmaceutical coating. Such a coating could be provided to provide sustained release of the pharmaceutical over a period of time. So, the stent could provide a pharmaceutical for initial treatment of a disease, and initially and in the longer term the stent gives a therapeutic benefit due to the characteristics which it imparts to the flow.

The stent may have a substantially circular cross-section and thus the smallest possible wetted perimeter to cross-sectional area ratio, whilst still having the necessary characteristics to induce swirl flow. Of course, there may be circumstances in which the stent has a non-circular cross-section, for example to assist interfacing or where pressure loss considerations are not significant.

The stent disclosed herein may be used in various biomedical applications e.g. in various arteries (such as in the coronary, carotid, lower limb and renal arteries), in veins, and in non-cardiovascular applications such as in the gastro-intestinal (e.g. bile or pancreatic ducts), genito-urinary (e.g. ureter or urethra) or the respiratory system (lung airways). Thus, the invention extends to stents for body fluids other than blood. In general, the use of the geometry of the invention can avoid the presence of stagnant regions, and hence be beneficial.

Certain preferred embodiments of the invention will now be described by way of example and with reference to the accompanying drawings, in which.

Figure 1:
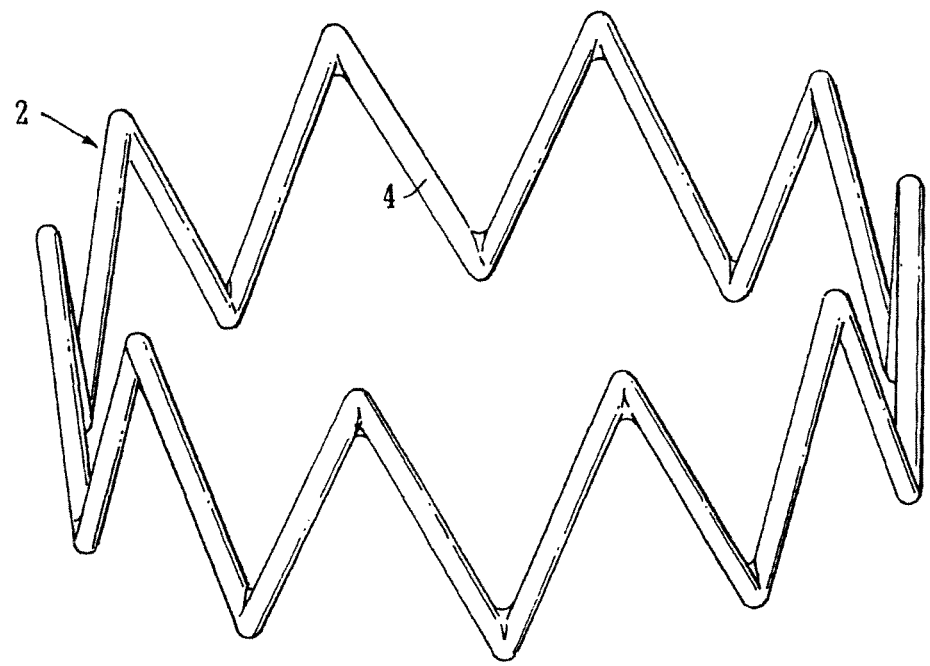
FIG. 1 is a perspective view of a tubular part of a stent.

FIG. 1 shows a tubular part 2 of a stent. The tubular part is a cylindrical structure in which a side wall of the structure is defined by bars 4 arranged in a zig-zag configuration. The tubular part extends circumferentially and is one form of circumferential part.

Figure 2:
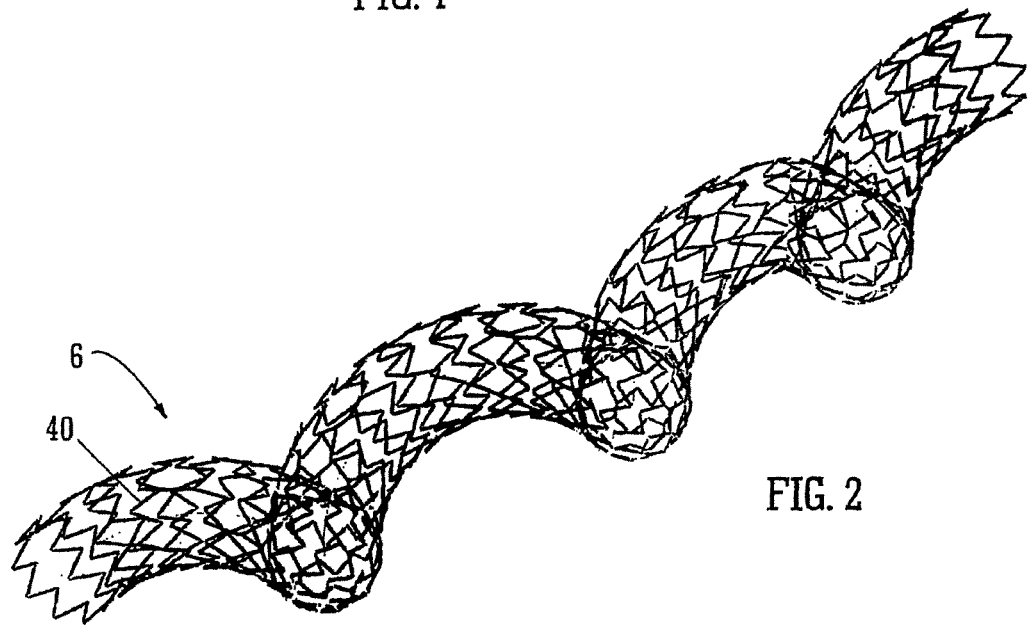
FIG. 2 is a perspective view of a helical stent including a series of tubular portions.

FIG. 2 shows a series of tubular parts 2 arranged side by side in a row so as to form a stent 6 of helical form. The stent has a helical centre line 40. The tubular parts 2 are interconnected by struts 8, as shown in FIG. 3 (the struts being omitted from FIG. 2 for clarity). Each tubular part 2 has opposite end portions 3a and 3b. Each end portion is in fact made up of the apexes of the zig-zag at a given end of the tubular part 2. Longitudinally adjacent tubular parts are arranged with their longitudinally facing end portions at an angle α to each other, i.e. they are not parallel as would be the case in a conventional cylindrical stent.

Figure 3A:
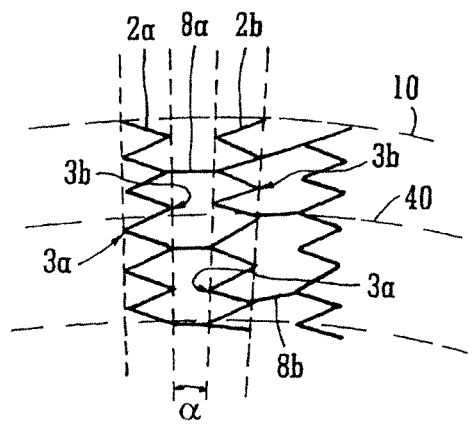
FIG. 3a is a side elevation view of part of the stent of FIG. 2.

In the part of the stent shown in FIG. 3a, a first tubular part 2a has longitudinal end portions 3a and 3b, whilst a second tubular part 2b similarly has longitudinal end portions 3a and 3b. The end portion 3b of the first tubular part 2a is longitudinally spaced from the end portion 3a of the second tubular part 2b. The lengths of the respective struts 8 differ so as to support the tubular parts 2a and 2b at the angle α relative to each other. A curve is thus introduced to a fluid conduit 10 supported by the stent.

A third tubular part 2c is positioned longitudinally adjacent to the second tubular part 2b and is connected thereto by another set of struts 8. This tubular part also lies at an angle α to tubular part 2b. However, the set of struts 8b is rotationally offset relative to the set of struts 8a, so that the stent will support the fluid conduit 10 to have a helical flow lumen.

The fluid conduit 10, supported by the stent 6 has a helical centre line 40 shown in FIGS. 2 and 3. The centre line of each tubular part 2a, 2b, 2c is arranged, by virtue of the struts 8, to lie on the centre line 40. Of course, because each tubular part 2 has a finite width in the longitudinal direction, this will be an approximation. The central plane across the width of each tubular part is intended to be normal to the tangent of the helical centre line 40 where it intersects that centre line.

Figure 3B:
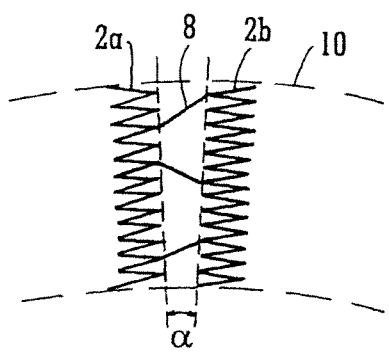
FIG. 3b is a side elevation view of a part of another stent.
Figure 3C:
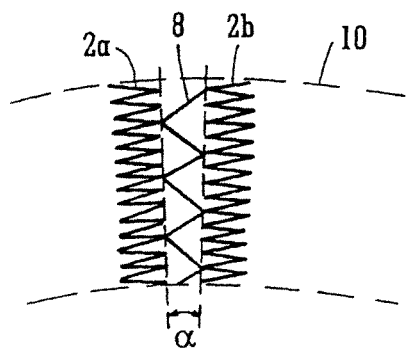
FIG. 3c is a side elevation view of a part of another stent.
Figure 3D:
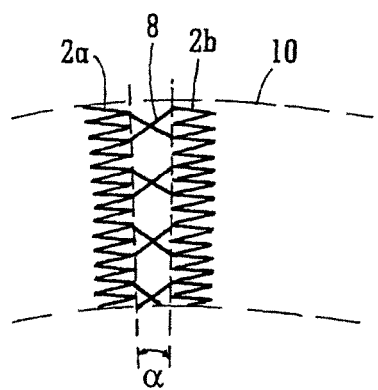
FIG. 3d is a side elevation view of a part of another stent.

FIGS. 3b, 3c and 3d show some alternative configurations of the struts 8, in which torsional stability is improved. The struts extend laterally as well as longitudinally, and some struts extend with a lateral component in one direction and other struts extend with a lateral component in an opposite direction. These arrangements of the struts are also suitable for joining the other circumferential parts described and shown herein.

FIG. 3b shows struts 8 where alternate struts have opposite lateral components, but the struts do not meet. In the embodiment of FIG. 3c, again alternate struts 8 have opposite lateral components, but they meet at their ends which join to the tubular parts 2. In FIG. 3d, pairs of struts 8 having opposite lateral component cross over mid-way of the longitudinal space between the tubular parts 2.

Figure 4:
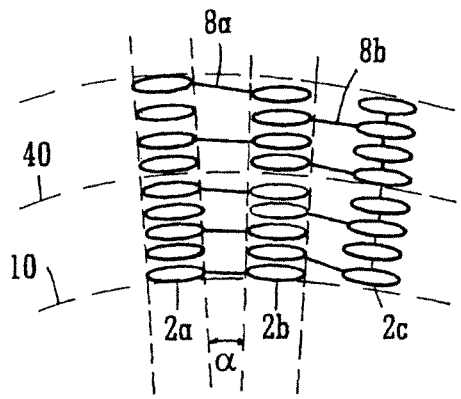
FIG. 4 is a side elevation view of a part of another stent.

FIG. 4 shows another stent design having tubular parts 2a, 2b and 2c interconnected by struts 8a and 8b. In this case the tubular parts are of a closed loop design. The same principles apply in obtaining a fluid conduit with a helical flow lumen.

Figure 5:
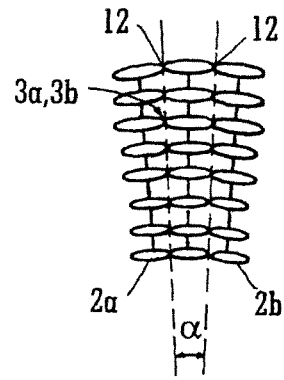
FIG. 5 is a side elevation view of a part of another stent.

In the stent of FIG. 5, a series of tubular parts are directly connected to each other at points 12, without the use of interconnecting struts 8. Thus the end portions 3a and 3b of longitudinally adjacent tubular parts 2a and 2b are joined together. In this case the opposite longitudinal end portions 3a, 3b of each individual tubular part are at an angle of α to each other. Longitudinally adjacent tubular parts are rotationally offset, in order to provide the stent with a helical centre line 40 and so as to be able to support a fluid conduit 10 with a helical flow lumen.

Figure 6:
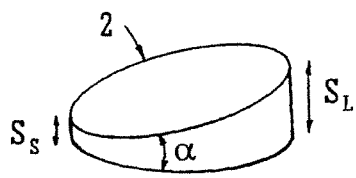
FIG. 6 is a schematic view of a tubular part of the stent of FIG. 5.
Figure 7:
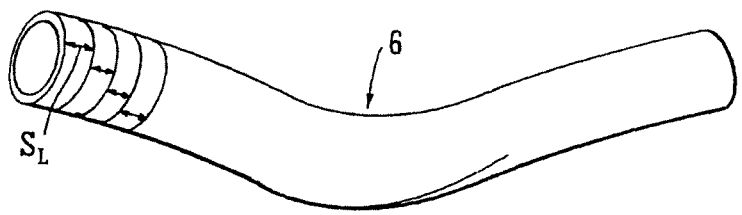
FIG. 7 is a schematic view of the stent of FIG. 5.

The stent of FIG. 5 is described further with reference to FIGS. 6 and 7. A tubular part 2 has one side having a length $S_L$ which is slightly longer than the length $S_s$ of the diametrically opposite side. To produce the stent with a helical curve, the tubular parts are connected together, with each part slightly rotated relative to the adjacent part. This is shown in FIG. 7. At the left hand end of the stent, the longer sides $S_L$ are shown for the first few parts, and it will be seen that there is relative rotation between the tubular parts. The amount of relative rotation determines the pitch of the helix, with a small relative rotation producing a helix with a small helix angle and a large pitch, and a large relative rotation producing a helix with a large helix angle and a small pitch.

It will be appreciated that at least one end of the tubular part will be somewhat elliptical, rather than perfectly circular, if the end is formed by the intersection of a plane cutting a cylinder at an angle to the axis of the cylinder which is not exactly 90°. However, given the general flexibility of the materials used to make stents, there will be some degree of compliance in the end portions of the tubular parts, so that they can accommodate the rotational offset and any necessary change in shape between the end portions being connected to each other.

Figure 8:
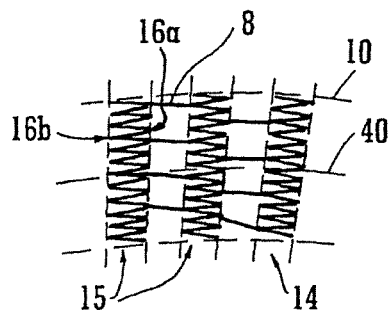
FIG. 8 is a side elevation view of a part of a stent having a continuous helical coil.
Figure 9:
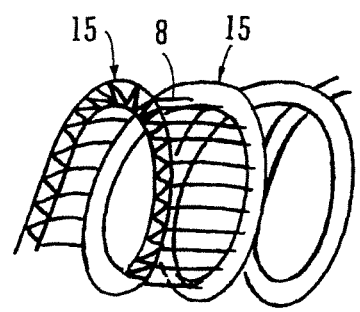
FIG. 9 is a schematic perspective view of the stent of FIG. 8.

FIGS. 8 and 9 show a stent made from a continuous helical coil, the helix angle of the coil being relatively large. It is known to make cylindrical stents using such a coiled arrangement. The coil 14 is made up a series of turns 15, each turn corresponding to a 360° winding of the helix, formed in this case by bars arranged in a zig-zag configuration. Each turn extends circumferentially and is a form of circumferential part. The coil 14 has a leading edge 16a and a trailing edge 16b, with the leading edge of one turn being longitudinally spaced from the trailing edge of an adjacent turn by connecting means in the form of struts 8. These struts are of different lengths in order to cause the centre line 40 of the coil 14 to follow a helix.

The struts 8 of FIGS. 3a, 4, 8 and 9 are shown as extending generally longitudinally. They may however take various configurations, for example having a lateral component as well as a longitudinal component, as shown in FIGS. 3b, 3c and 3d. Thus, in a given longitudinal direction, some of a set of struts forming the connecting means may have a lateral component to the left and others may have a lateral component to the right. This may assist with torsional stability, in effect ensuring that the expanded stent adopts the desired non-planar shape.

Figure 10:
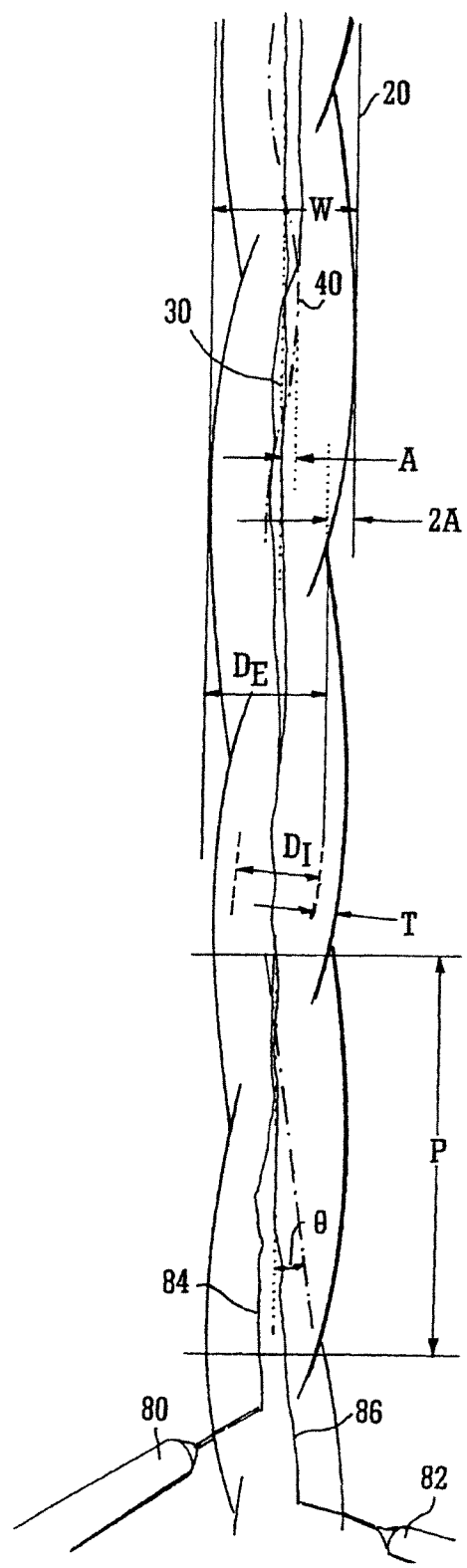
FIG. 10 is an elevation of tubing having a helical flow lumen.

The tubing 1 shown in FIG. 10 shows a possible shape of a fluid conduit as imposed by a stent of the present invention. The tubing has a circular cross-section, an external diameter $D_E$, an internal diameter $D_I$ and a wall thickness T. The tubing is coiled into a helix of constant amplitude A (as measured from mean to extreme), constant pitch P, constant helix angle θ and a swept width W. The tubing part 1 is contained in an imaginary envelope 20 which extends longitudinally and has a width equal to the swept width W of the helix. The envelope 20 may be regarded as having a central longitudinal axis 30, which may also be referred to as an axis of helical rotation. The illustrated tubing 1 has a straight axis 30, but it will be appreciated that in alternative designs the central axis may be curved. The tubing has a centre line 40 which follows a helical path about the central longitudinal axis 30.

It will be seen that the amplitude A is less than the tubing internal diameter $D_I$. By keeping the amplitude below this size, the space occupied by the tubing can be kept relatively small, whilst at the same time the helical configuration of the tubing promotes swirl flow of fluid along the tubing.

EXAMPLE 1

Experiments were carried out using polyvinyl chloride tubing with a circular cross-section. Referring to the parameters shown in FIG. 10 the tubing had an external diameter $D_E$ of 12 mm, an internal diameter $D_I$ of 8 mm and a wall thickness T of 2 mm. The tubing was coiled into a helix with a pitch P of 45 mm and a helix angle θ of 8°. The amplitude A was established by resting the tubing between two straight edges and measuring the space between the straight edges. The amplitude was determined by subtracting the external to diameter $D_E$ from the swept width W:

$$2A = W - D_E$$

So:

$$A = \frac{W - D_E}{2}$$

In this example the swept width W was 14 mm, so:

$$A = \frac{W - D_E}{2} = \frac{14 - 12}{2} = 1 \text{ mm}$$

As discussed earlier, "relative amplitude" $A_R$ is defined as:

$$A_R = \frac{A}{D_I}$$

In the case of this Example, therefore:

$$A_R = \frac{A}{D_I} = \frac{1}{8} = 0.125$$

Water was passed along the tube. In order to observe the flow characteristics, two needles 80 and 82 passing radially through the tube wall were used to inject visible dye into the flow. The injection sites were near to the central axis 30, i.e. at the "core" of the flow. One needle 80 injected red ink and the other needle 82 blue ink.

Figure 11:
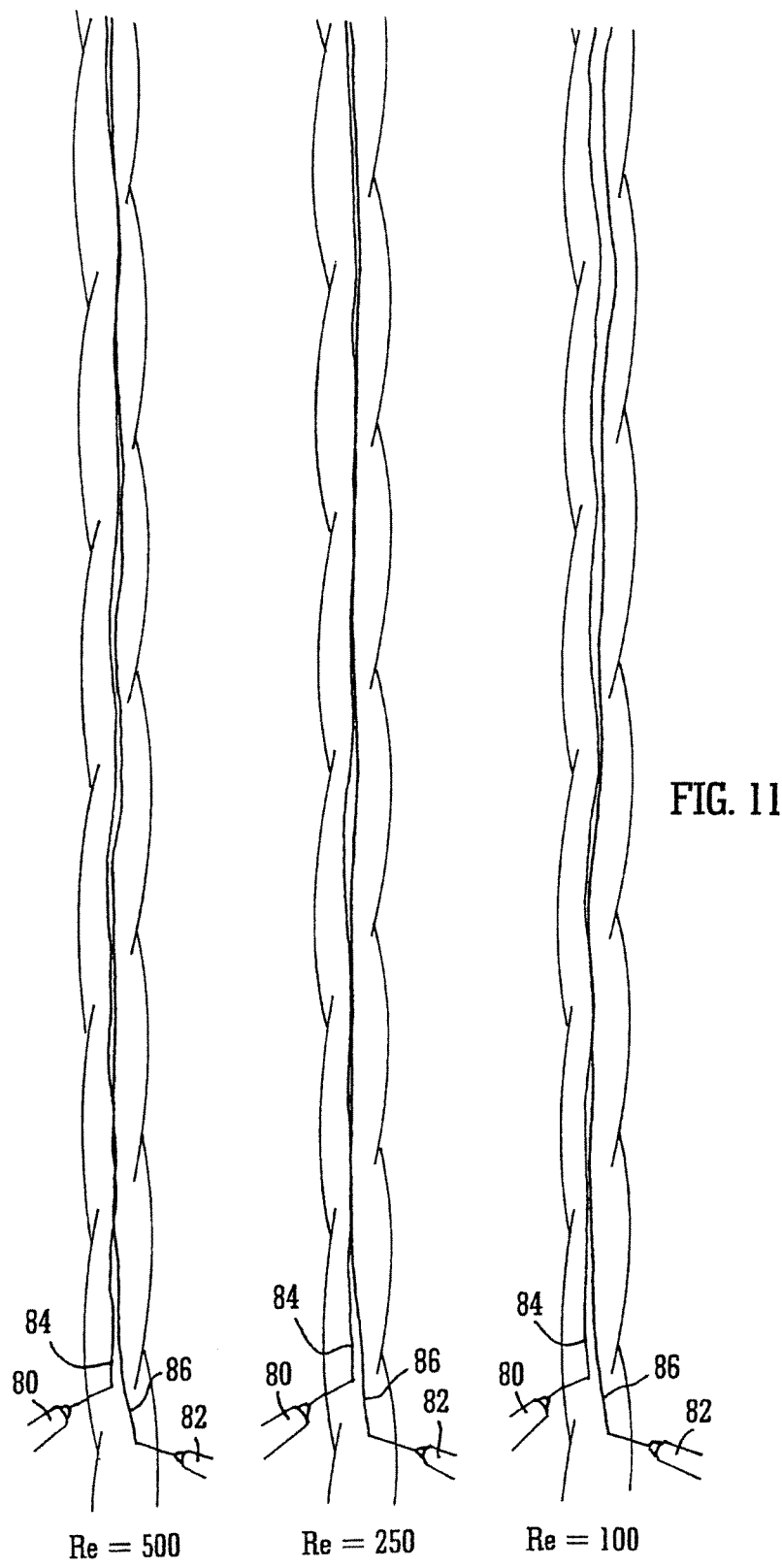
FIG. 11 shows elevation views of tubings used in experiments.

FIG. 11 shows the results of three experiments, at Reynolds numbers $R_E$ of 500, 250 and 100 respectively. It will be seen in all cases that the ink filaments 84 and 86 intertwine, indicating that in the core there is swirl flow, i.e. flow which is generally rotating.

EXAMPLE 2

Figure 12:
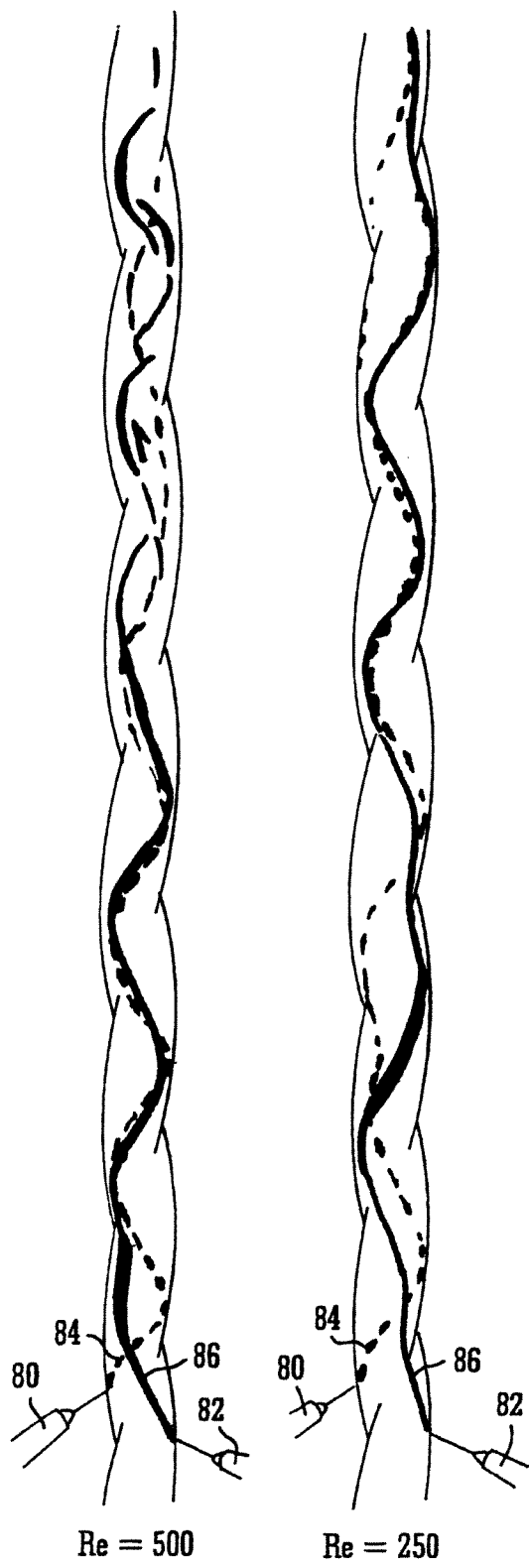
FIG. 12 shows elevation views of tubings used in further experiments.

The parameters for this Example were the same as in Example 1, except that the needles 80 and 82 were arranged to release the ink filaments 84 and 86 near to the wall of the tubing. FIG. 12 shows the results of two experiments with near-wall ink release, with Reynolds numbers $R_E$ of 500 and 250 respectively. It will be seen that in both cases the ink filaments follow the helical tubing geometry, indicating near-wall swirl. Furthermore, mixing of the ink filaments with the water is promoted.

Preferred stents have values of relative amplitude $A_R$ less than or equal to 0.5, i.e. small relative amplitudes. In a straight stent both the amplitude A and the relative amplitude $A_R$ equal zero, as there is no helix. Therefore, with values of relative amplitude $A_R$ approaching zero, the ability of the stent to induce swirl will reduce. The lowest workable value of relative amplitude $A_R$ for any given situation will depend on the speed of flow and the viscosity and density of the fluid (i.e. Reynolds number) and on the pitch (helix angle) and the particular use of the stent. Relative amplitudes of at least 0.05, 0.10, 0.15, 0.20, 0.25, 0.30, 0.35, 0.40 or 0.45 may be preferred.

The invention claimed is:

1. A stent for insertion in a fluid conduit of a human or animal body, comprising a hollow structure, the hollow structure having an interior, wherein the interior is free of grooves, ridges, ribs or vanes, the hollow structure having a center line, a longitudinal direction and a length, and having circumferentially extending parts which have opposite end portions in the longitudinal direction, the circumferentially extending parts being joined to longitudinally adjacent circumferentially extending parts along the length of the hollow structure, wherein a set of struts connects adjacent circumferentially extending parts to each other, wherein the set of struts includes first and second struts both connecting the same adjacent circumferentially extending parts, the first strut having a portion being oriented in a first lateral direction as well as longitudinally and the second strut having a portion being oriented in a second lateral direction opposite to the first lateral direction as well as longitudinally, wherein in use the adjacent end portions of adjacent circumferentially extending parts are not in parallel planes, and wherein in use, the center line of the hollow structure follows a helical path which undergoes more than one turn, whereby a flow lumen defined by the hollow structure and imposed on the fluid conduit by the hollow structure when in the fluid conduit, extends helically in the longitudinal direction and wherein each circumferentially extending part has a centroid and the centroids of the circumferentially extending parts follow a helical path.

2. A stent as claimed in claim 1, wherein the circumferentially extending parts are tubular parts.

3. A stent as claimed in claim 2, wherein the tubular parts are longitudinally spaced from each other and joined together by the set of struts.

4. A stent as claimed in claim 1, wherein the circumferentially extending parts are turns belonging to a single helical coil extending circumferentially and longitudinally of the hollow structure.

5. A stent as claimed in claim 4, wherein the turns are longitudinally spaced from each other and joined together by the set of struts.

6. A stent as claimed in claim 1, wherein the set of struts connecting adjacent circumferentially extending parts includes a strut having a long length which is located on one side of the hollow structure and another strut having a short length which is located on a diametrically opposite side of the hollow structure,
  and wherein the long strut is rotationally offset from a long strut of a set of struts connecting longitudinally adjacent circumferentially extending parts.

7. A stent as claimed in claim 1, wherein the hollow structure has a circumference, and the set of struts comprises a plurality of struts including first and second struts arranged around the circumference of the hollow structure.

8. A stent as claimed in claim 1, wherein the first and second struts cross over each other.

9. A stent as claimed in claim 1, wherein an end of the first strut is disposed adjacent to an end of the second strut.

10. A stent for insertion in a fluid conduit of a human or animal body, comprising a hollow structure the hollow structure having an interior, wherein the interior is free of grooves, ridges, ribs or vanes, the hollow structure having a center line, a longitudinal direction and a length, and having circumferentially extending parts which have opposite end portions in the longitudinal direction, the circumferentially extending parts being joined to longitudinally adjacent circumferentially extending parts along the length of the hollow structure, wherein in use adjacent end portions of adjacent circumferentially extending parts are not in parallel planes, and wherein in use, the center line of the hollow structure follows a helical path which undergoes more than one turn, whereby a flow lumen defined by the hollow structure and imposed on the fluid conduit by the hollow structure when in the fluid conduit, extends helically in the longitudinal direction and wherein each circumferentially extending part has a centroid and the centroids of the circumferentially extending parts follow a helical path.

11. A stent as claimed in claim 10, wherein the circumferentially extending parts are tubular parts.

12. A stent as claimed in claim 11, wherein the tubular parts are joined together by a set of struts.

13. A stent as claimed in claim 12, wherein the set of struts connecting adjacent circumferentially extending parts includes a strut having a long length which is located on one side of the hollow structure and another strut having a short length which is located on a diametrically opposite side of the hollow structure,
  and wherein the long strut is rotationally offset from a long strut of a set of struts connecting longitudinally adjacent circumferentially extending parts.

* * * * *